(12) United States Patent
Katsuda et al.

(10) Patent No.: US 7,712,349 B2
(45) Date of Patent: May 11, 2010

(54) GAS SENSOR

(75) Inventors: Hayato Katsuda, Aichi (JP); Youichi Hattori, Aichi (JP); Yuichi Kouyama, Aichi (JP); Takio Kojima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 44 days.

(21) Appl. No.: 10/581,075

(22) PCT Filed: Dec. 1, 2004

(86) PCT No.: PCT/JP2004/017884

§ 371 (c)(1),
(2), (4) Date: Aug. 29, 2006

(87) PCT Pub. No.: WO2005/054835

PCT Pub. Date: Jun. 16, 2005

(65) Prior Publication Data

US 2007/0107493 A1    May 17, 2007

(30) Foreign Application Priority Data

Dec. 1, 2003  (JP)  ............................. 2003-401382
Dec. 1, 2003  (JP)  ............................. 2003-401386

(51) Int. Cl.
*G01N 9/00*     (2006.01)
(52) U.S. Cl. .................................... 73/31.05; 73/23.31
(58) Field of Classification Search ................. 204/431; 73/31.05

See application file for complete search history.

(56) References Cited

U.S. PATENT DOCUMENTS 5,624,639 A    4/1997   Ariga et al.

(Continued)

FOREIGN PATENT DOCUMENTS

JP          57-28245 A    2/1982

(Continued)

*Primary Examiner*—Hezron Williams
*Assistant Examiner*—Mark Shabman
(74) *Attorney, Agent, or Firm*—Sughrue Mion, PLLC

(57) ABSTRACT

The object of the present invention is to provide a gas sensor in which a gas detection element is mounted on a wiring substrate; in which a protective cap having gas inlets formed therein is attached to the wiring substrate; and which has a structure capable of effectively preventing emanation of gas from the wiring substrate and the protective cap. A gas sensor comprises a gas detecting element on a writing board where a protective cap with air vents is mounted. The sensor effectively prevents a gas from emanating from the wiring board and the protective cap. The wiring board where a plurality of gas detecting elements (8,9) are to be mounted is formed of a ceramic wiring board (2) excellent in heat resistance. The protective cap (3) having air vents (31 to 39) is formed of a metal excellent in heat resistance. The metal protective cap (3) is fitted to the ceramic wiring board (2) instead of using adhesive. In this way a gas sensor (1) is manufactured. Adoption of such a structure enables suppression of the gas emission from the ceramic wiring board (2) and the metal protective cap (3) effectively during the manufacturing step or in use of the gas sensor (1) attached to a car, thereby preventing lowering of the gas detection accuracy or early deterioration of the gas detecting elements (8,9).

8 Claims, 11 Drawing Sheets

U.S. PATENT DOCUMENTS

| | | | |
|---|---|---|---|
| 6,893,892 B2 * | 5/2005 | Gole et al. | 438/48 |
| 2003/0188968 A1 * | 10/2003 | Naito et al. | 204/424 |
| 2005/0081603 A1 * | 4/2005 | Gehman et al. | 73/31.07 |

FOREIGN PATENT DOCUMENTS

| | | |
|---|---|---|
| JP | 61-112259 U | 7/1986 |
| JP | 64-6833 A | 1/1989 |
| JP | 2-52150 U | 4/1990 |
| JP | 6-31415 | 8/1994 |
| JP | 7-32559 U | 6/1995 |
| JP | 8-97318 A | 4/1996 |
| JP | 8-192617 A | 7/1996 |
| JP | 9-21774 A | 1/1997 |
| JP | 921774 * | 1/1997 |
| JP | 9-264864 A | 10/1997 |
| JP | 10-12808 A | 1/1998 |
| JP | 10-111265 A | 4/1998 |
| JP | 11-190710 A | 7/1999 |
| JP | 11-233240 | 8/1999 |
| JP | 2001-66282 A | 3/2001 |
| JP | 2001-119169 A | 4/2001 |
| JP | 2001-175970 A | 6/2001 |
| JP | 2002-168819 A | 6/2002 |
| JP | 2002-174608 A | 6/2002 |
| JP | 2002-286674 A | 10/2002 |
| JP | 2003-83932 A | 3/2003 |
| JP | 2003-329642 A | 11/2003 |
| JP | 2004-55959 A | 2/2004 |

* cited by examiner

[Fig.1]
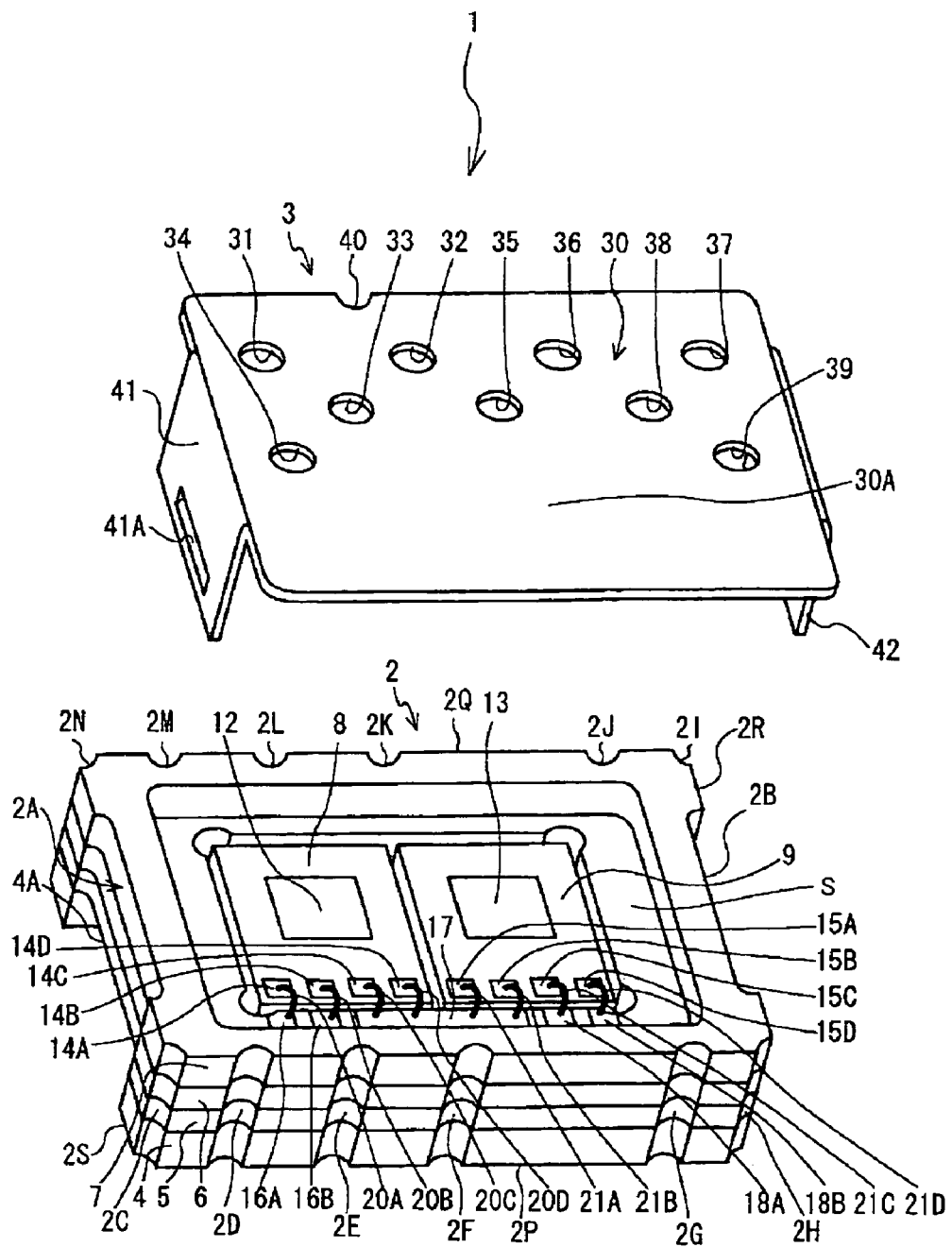

[Fig.2]
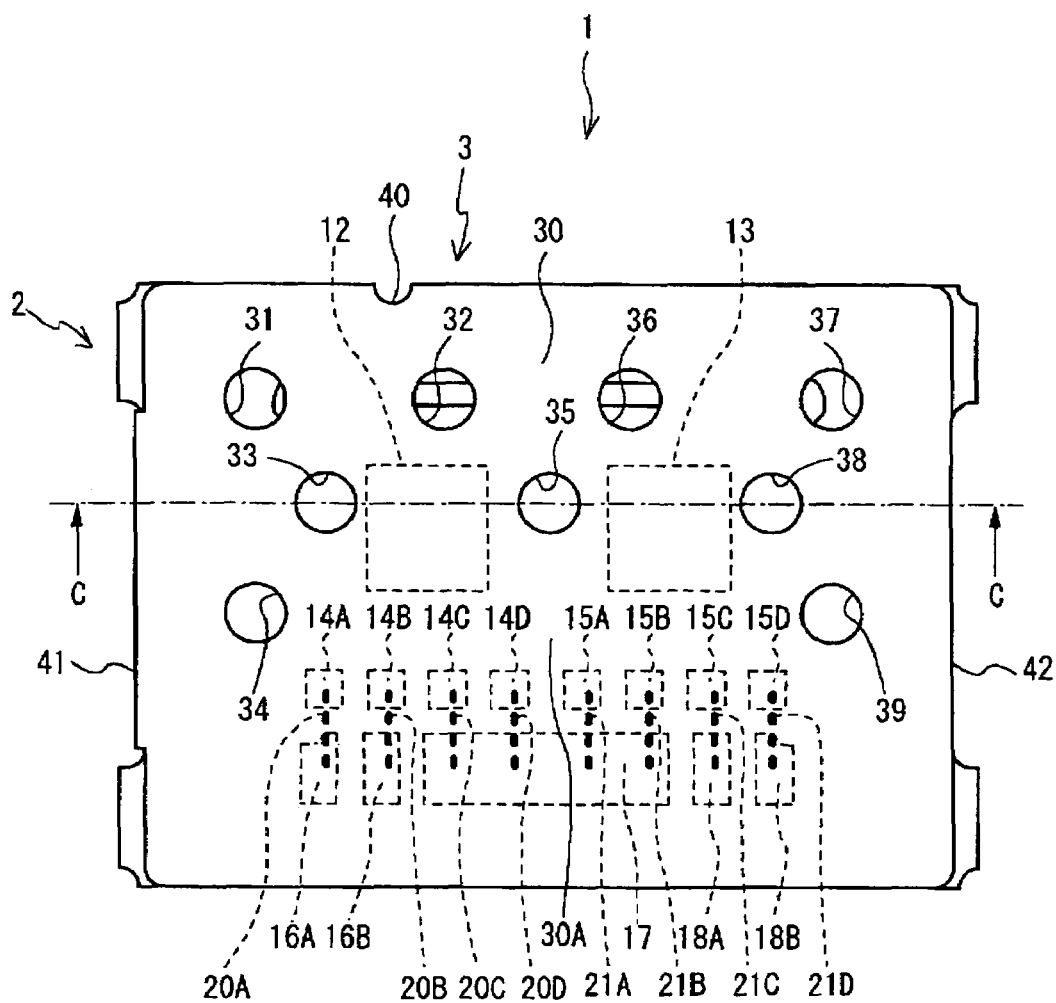

[Fig.3]
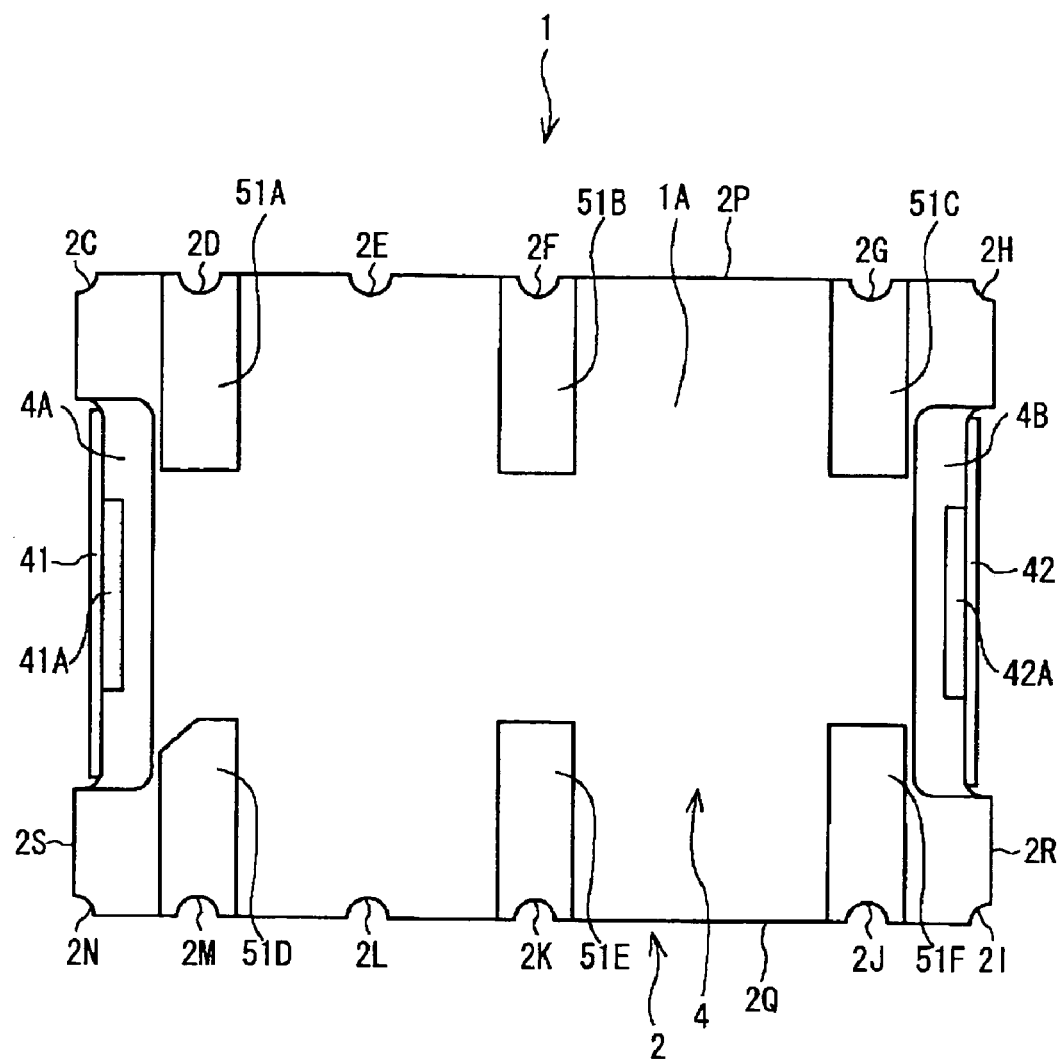

[Fig. 4]
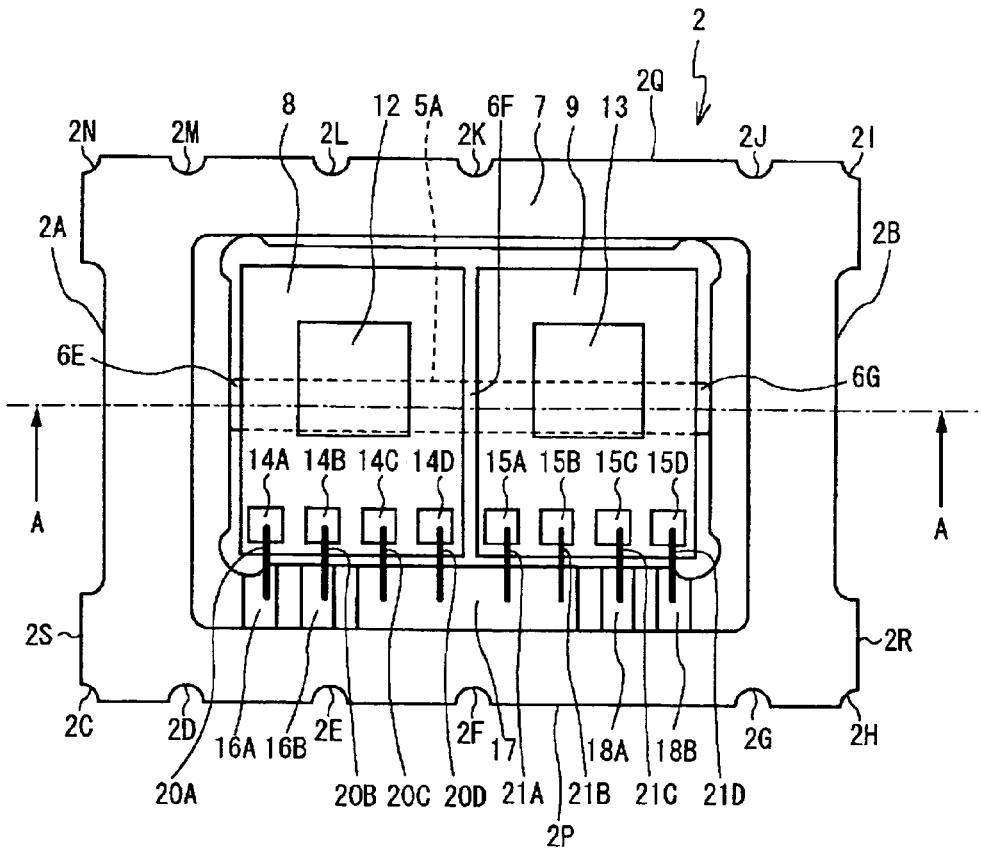
[Fig. 5]
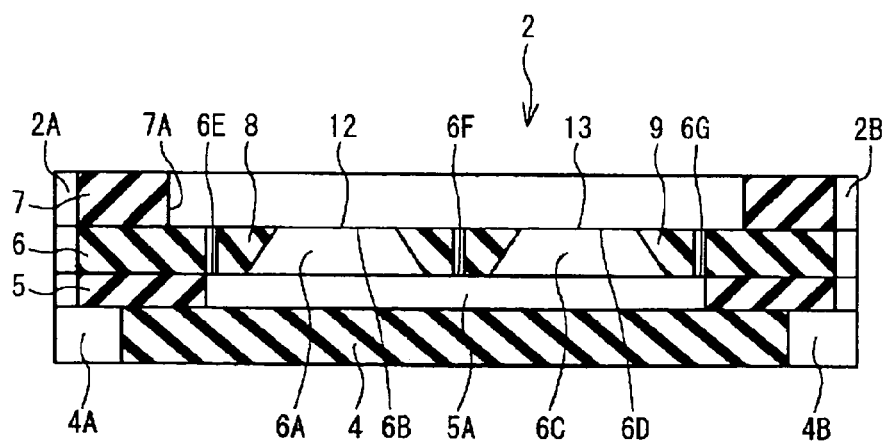

[Fig.6]
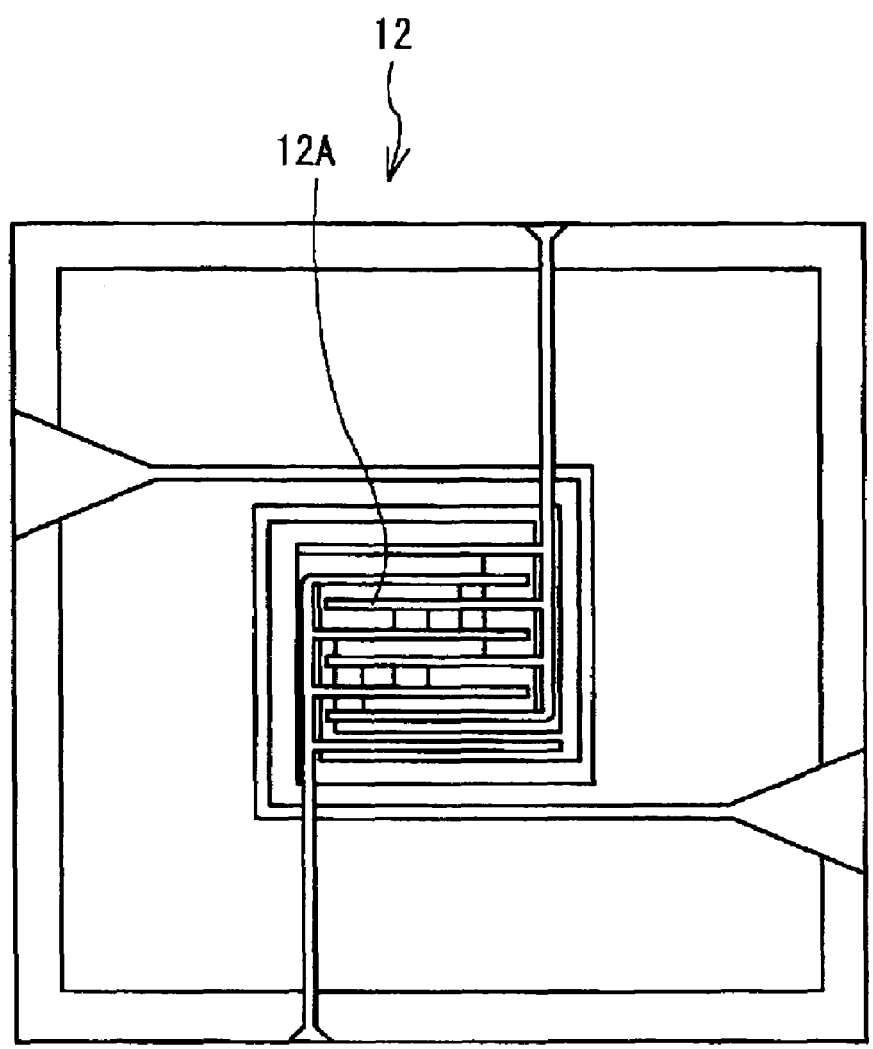

[Fig.7]
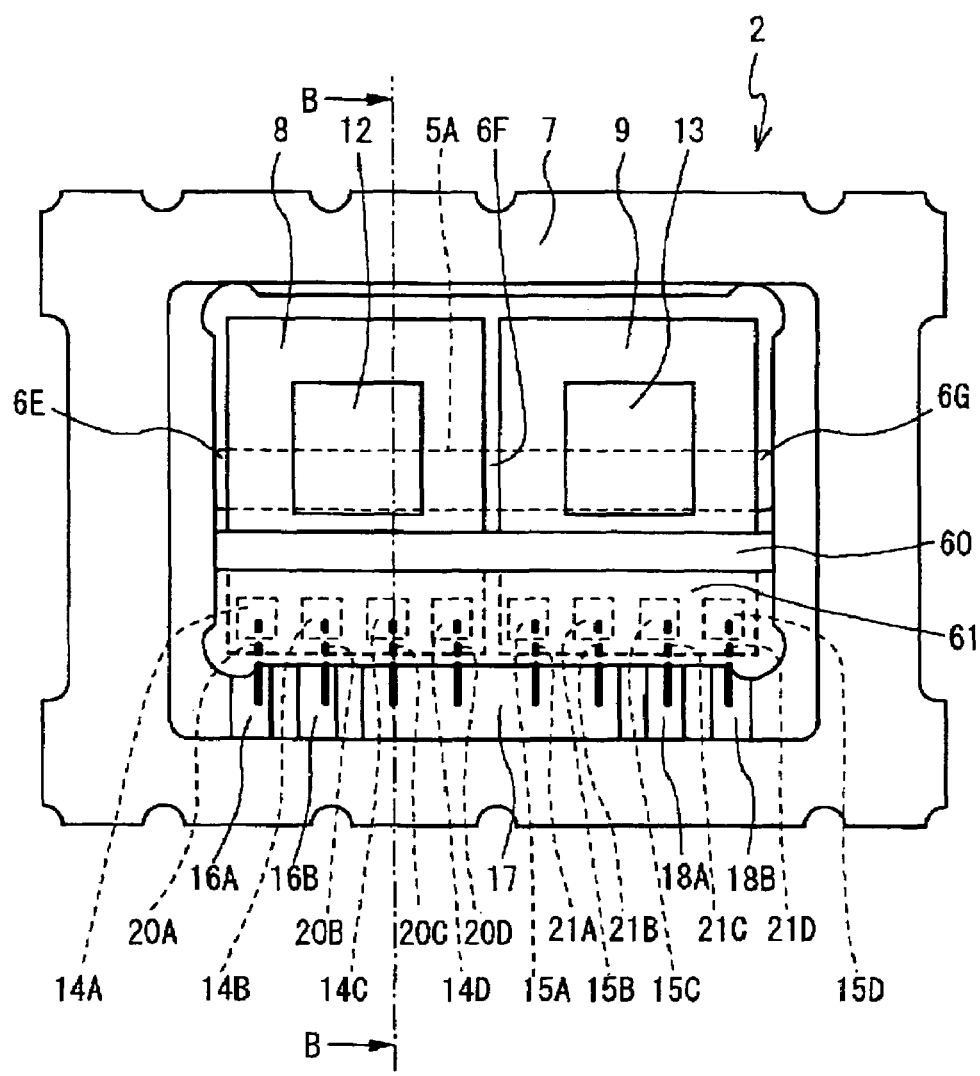

[Fig.8]
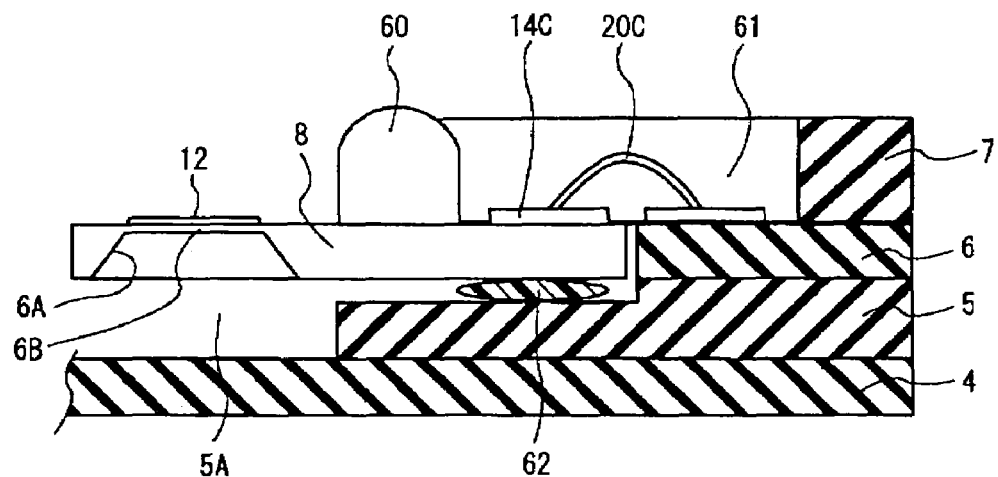

[Fig.9]
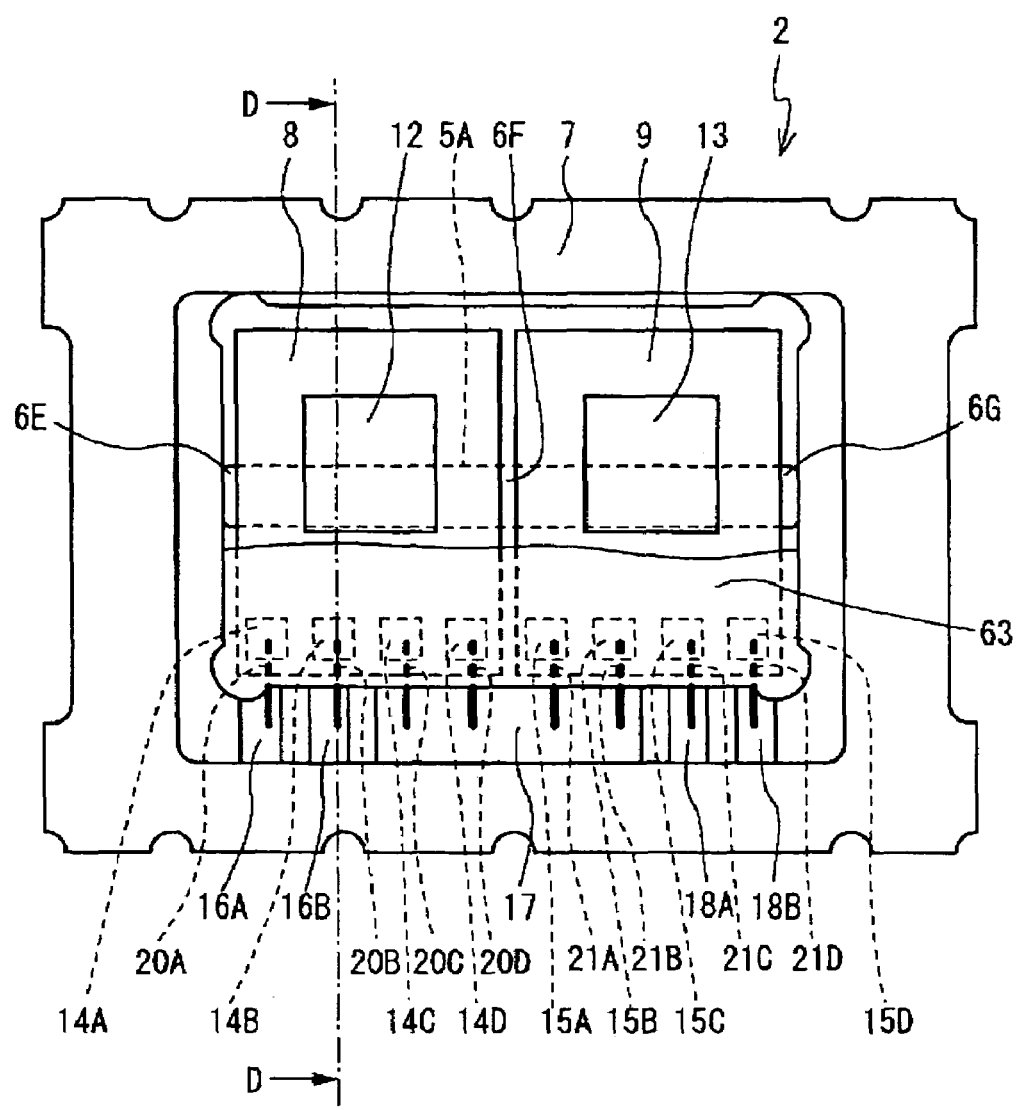

[Fig.10]
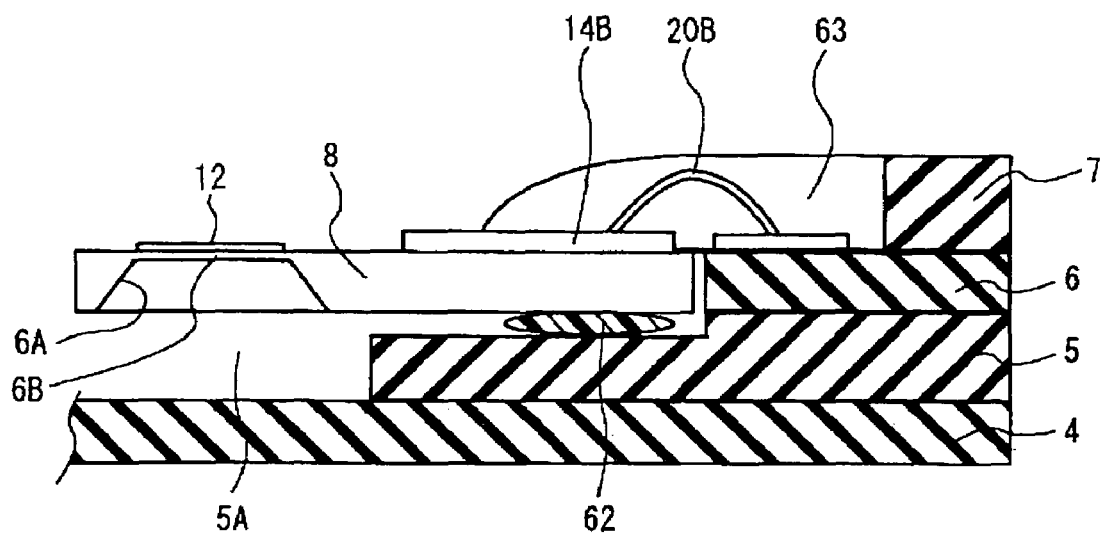

[Fig.11]
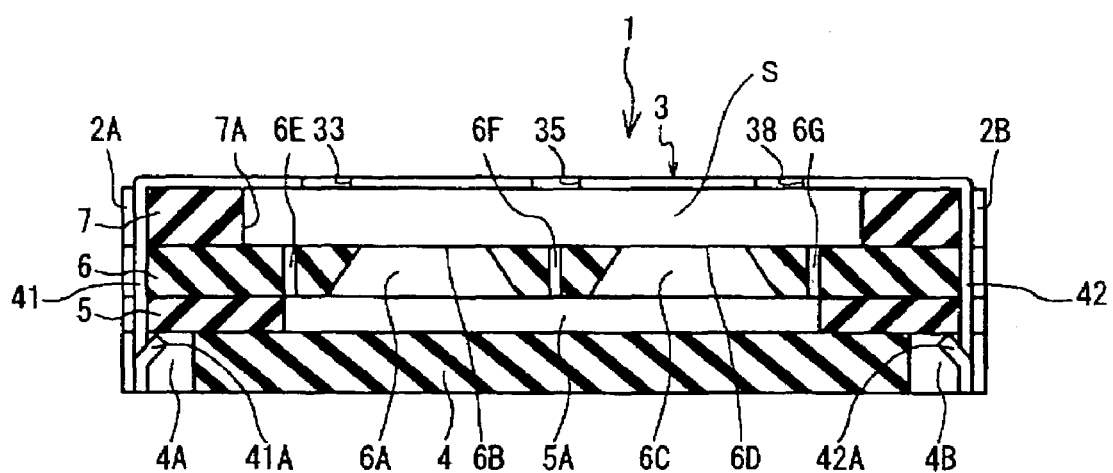

[Fig.12]
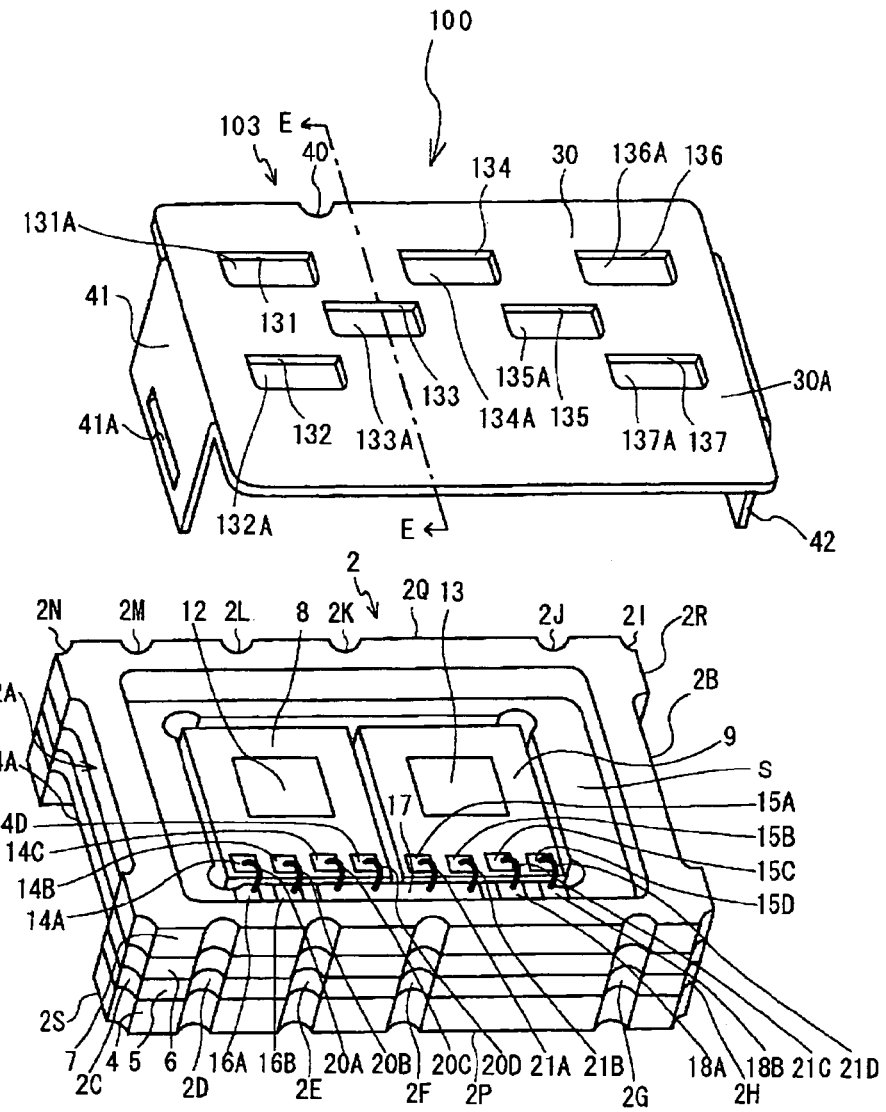
[Fig.13]

_GAS SENSOR_

TECHNICAL FIELD

The present invention relates to a gas sensor in which a gas detection element is mounted on a wiring substrate which serves as a support member. Particularly, the present invention is usefully applied to a gas sensor in which a gas detection element having a diaphragm structure section which is formed by use of silicon micromachining technology is mounted on a wiring substrate.

BACKGROUND ART

A conventionally known gas sensor is configured such that a gas detection element (microsensor chip) is mounted on a package (wiring substrate) on which terminals for input from and output to an external circuit are formed and such that a cover in which a plurality of gas inlets are formed for introducing therethrough a gas to be measured is fixedly attached to a perimetric frame of the package (refer to, for example, Patent Document 1). Another conventionally known gas sensor is configured such that a gas detection element is held via a lead frame in a suspended condition by a quadrangular, tubular fixation element and such that the fixation element is fixedly covered at its top face with a cover element in which a plurality of gas inlets are formed for introducing therethrough a gas to be measured, and at its bottom face with a shield cover element (refer to, for example, Patent Document 2).

Patent Document 1: Japanese Patent Application Laid-Open (kokai) No. H11-233240
Patent Document 2: Japanese Patent Application Laid-Open (kokai) No. H09-21774

DISCLOSURE OF THE INVENTION

Problems to be Solved by the Invention

Conventionally, resin is used to form a package on which a gas detection element is mounted and which is typified by those of Patent Documents 1 and 2. Particularly, in Patent Document 2, resin is also used to form even the two cover elements which are fixedly attached to the corresponding opposite sides of the package. However, when the package made of resin is used, in the process of manufacture of the gas sensor or in use of the gas sensor attached to an automobile, the resin used to form the package may emanate gas, since the gas sensor may be exposed to a high-temperature environment of, for example, 200° C. to 300° C.

When a component gas (e.g., silicon gas) contained in the thus-emanated gas adheres to the gas detection element, there is risk of a drop in gas detection accuracy. Particularly, in the case of a gas detection element which uses a metal oxide semiconductor as a gas detection portion, adsorption of a component gas contained in the thus-emanated gas on the surface of the gas detection portion may cause not only a drop in gas detection accuracy, but also early deterioration of the performance of the gas detection element.

The present invention has been accomplished in view of the foregoing, and an object of the present invention is to provide a gas sensor in which a gas detection element is mounted on a wiring substrate; in which a protective cap having gas inlets formed therein is attached to the wiring substrate; and which has a structure capable of effectively preventing emanation of gas from the wiring substrate and the protective cap to thereby maintain good gas detection accuracy over a long period of time.

MEANS FOR SOLVING THE PROBLEMS

Means for solving the problems is a gas sensor comprising a gas detection element; a ceramic wiring substrate on which the gas detection element is mounted; and a protective cap which is attached to the ceramic wiring substrate in such a manner as to cover the gas detection element and which is made of metal, defines, when attached to the ceramic wiring substrate, a gas-measuring space in cooperation with the ceramic wiring substrate, and has a gas intake for introducing a gas to be measured into the gas-measuring space from the outside thereof.

In the gas sensor of the present invention, the wiring substrate assumes the form of a ceramic wiring substrate having excellent heat resistance, and the protective cap having the gas intake is formed of a metal having excellent heat resistance. Accordingly, in the process of manufacture of the gas sensor or in use of the gas sensor attached to an automobile, emanation of gas from the ceramic wiring board and the metal protective cap can be effectively suppressed, thereby preventing a drop in gas detection accuracy or early deterioration of the gas detection element.

In contrast to a conventional gas sensor which employs a resin package and a resin protective cap, the gas sensor of the present invention employs the ceramic wiring substrate and the metal protective cap, which exhibit excellent heat resistance. Thus, even when exposed to a high-temperature environment over a long period of time, the gas sensor of the present invention is unlikely to be deformed. Also, from this point of view, reliability can be improved.

Alumina, mullite, silicon nitride, aluminum nitride, or a like material can be used as ceramic for constituting the ceramic wiring substrate. In view of eminent attainment of heat resistance and dielectric performance, use of alumina is preferred.

No particular limitation is imposed on the form of the gas intake formed in the protective cap. The gas intake may be a through hole, or a linear slit which is formed in the outer wall of the protective cap such that a portion of the outer wall extending from the slit projects toward the gas-measuring space while being integral at its one end with the outer wall, thereby establishing communication between the outside of the gas sensor and the gas-measuring space. Further, the number of gas intakes may be one or more than one.

Preferably, in the above-described gas sensor, the protective cap is held on the ceramic wiring substrate in a nonadhering condition.

Conventionally, in many cases, in fixation of a package (wiring substrate) and a protective cap to each other, the protective cap is bonded to the outer frame of the package in a sealed condition by use of adhesive. However, the case where the wiring substrate and the protective cap are fixed together by use of adhesive involves the risk of gas emanation also from the adhesive, resulting in a drop in detection accuracy of the gas detection element.

By contrast, in the gas sensor of the present invention, the protective cap is held on the ceramic wiring substrate in a nonadhering condition without use of adhesive, thereby preventing gas emanation which could otherwise result from adhesive. By virtue of employment of the fixation feature combined with the effect of employment of the ceramic wiring substrate and the metal protective cap, a drop in gas detection accuracy or early deterioration of the gas detection element can be prevented with higher reliability. Notably, methods for holding the protective cap on the ceramic wiring substrate in a nonadhering condition include fit engagement and press fit.

Preferably, in the above-described gas sensor, the ceramic wiring substrate has a multilayer structure in which a plurality of ceramic dielectric layers are laminated; a recess is formed on a portion of a side surface of the ceramic wiring substrate which corresponds to a side surface of a ceramic dielectric layer other than an uppermost ceramic dielectric layer which forms a top surface of the ceramic wiring substrate; the protective cap has a perpendicularly projecting portion extending along the side surface of the ceramic wiring substrate; and an engagement projection to be fitted into the recess is formed on the perpendicularly projecting portion.

In order to hold the protective cap on the ceramic wiring substrate in a nonadhering condition, the gas sensor of the present invention employs the following structure: the recess is formed on a portion of a side surface of the ceramic wiring substrate which corresponds to a side surface of a layer other than the uppermost layer which forms the top surface of the ceramic wiring substrate, and the engagement projection formed on the perpendicularly projecting portion of the protective cap is fitted into the recess. This structure enables the protective cap to be stably held on the ceramic wiring substrate. By virtue of easy attachment of the protective cap to the ceramic wiring substrate, the gas sensor of the present invention offers an advantage that a step of attaching the protective cap to the ceramic wiring substrate becomes less complicated.

Preferably, in the above-described gas sensor, the ceramic wiring substrate has a substantially quadrangular shape as viewed along the direction of lamination of the multilayer structure, and the recess is formed on each of at least two opposed side surfaces of the ceramic wiring substrate.

In the gas sensor of the present invention, the recess is formed on at least two opposed side surfaces of the ceramic wiring substrate having a substantially quadrangular shape, and the engagement projections of the perpendicularly projecting portions of the protective cap are fitted into the corresponding recesses, whereby the protective cap can be reliably fixed to the ceramic wiring substrate.

Preferably, in the above-described gas sensor, a guide recess is formed on the side surfaces of the ceramic wiring substrate so as to guide the perpendicularly projecting portions to locations where the engagement projections are fitted into the corresponding recesses.

In the gas sensor of the present invention, the guide recesses are formed on the corresponding side surfaces of the ceramic wiring substrate and smoothly guide the perpendicularly projecting portions of the protective cap to locations where the engagement projections are fitted into the corresponding recesses, thereby facilitating fixation of the protective cap to the ceramic wiring substrate and preventing erroneous attachment of the protective cap.

Preferably, in the above-described gas sensor, the gas detection element includes a diaphragm structure section, and the diaphragm structure section includes a gas detection portion; the protective cap has a plurality of the gas intakes formed in a ceiling portion in opposition to a mounting surface of the ceramic wiring substrate on which the gas detection element is mounted; and the plurality of gas intakes are formed such that when the gas intakes are viewed from the outside of the ceiling portion along a direction perpendicular to the mounting surface, the diaphragm structure section of the gas detection element is invisible therethrough.

In recent years, there has been known a gas detection element configured such that a gas detection portion is formed on a diaphragm structure section which is formed by use of silicon micromachining technology. In the gas detection element of this structure, the diaphragm structure section assumes the form of a thin sheet, thereby thermally isolating the gas detection portion and the body of a silicon substrate from each other. Thus, the gas detection element has an advantage that gas detection accuracy can be enhanced. Application of a gas detection element having such a diaphragm structure section to the above-mentioned gas sensor involves the following problems: when foreign matter which has entered through the gas intakes impinges on the diaphragm structure section, not only does the performance of the gas detection element drop, but also the diaphragm structure section in the form of a thin sheet is damaged.

By contrast, in the gas sensor of the present invention, the plurality of gas intakes are formed such that when the gas intakes are viewed from the outside of the ceiling portion along a direction perpendicular to the mounting surface of the ceramic wiring substrate on which the gas detection element is mounted; i.e., when the plurality of gas intakes are viewed from above the ceiling portion along the direction perpendicular to the mounting surface, the diaphragm structure section of the gas detection element is invisible therethrough. By virtue of this structural feature, foreign matter which has entered through the gas intakes is unlikely to adhere to the gas detection portion formed on the diaphragm structure section. Also, foreign matter is unlikely to directly impinge on the diaphragm structure section through the gas intakes, thereby effectively preventing damage to the diaphragm structure section which could otherwise result from impingement of foreign matter.

Preferably, in the above-described gas sensor, element-side electrodes are provided on the gas detection element; substrate-side electrodes are provided on the ceramic wiring substrate; connection portions are provided for connecting the element-side electrodes and the corresponding substrate-side electrodes; and the plurality of gas intakes are formed such that when the gas intakes are viewed from the outside of the ceiling portion along a direction perpendicular to the mounting surface, the connection portions are invisible therethrough.

In the gas sensor of the present invention, the plurality of gas intakes are formed such that when the gas intakes are viewed from the outside of the ceiling portion along a direction perpendicular to the mounting surface of the ceramic wiring substrate on which the gas detection element is mounted; i.e., when the plurality of gas intakes are viewed from above the ceiling portion along the direction perpendicular to the mounting surface, the connection portions connecting the element-side electrodes and the substrate-side electrodes are invisible via the gas intakes. By virtue of this structural feature, foreign matter which has entered through the gas intakes is unlikely to adhere to the connection portions. Also, a short circuit between conductor lines of the connection portions, which could otherwise be caused by foreign matter, can be prevented.

Preferably, in the above-described gas sensor, the gas detection element includes the diaphragm structure section, and the diaphragm structure section includes the gas detection portion; the ceramic wiring substrate has a multilayer structure in which a plurality of ceramic dielectric layers are formed such that inner wiring layers are sandwiched therebetween; and a recess is formed on the ceramic dielectric layer among the plurality of ceramic dielectric layers on which the gas detection element is mounted, in a region in opposition to the diaphragm structure section.

As mentioned previously, in recent years, a gas detection element in which a gas detection portion is formed on a diaphragm structure section has been marketed. In the case of such a gas detection element having the diaphragm structure, when the gas detection portion undergoes heating control which is performed by use of a microheater or the like formed in the diaphragm structure section, the internal pressure of the diaphragm structure section increases, potentially causing damage to the diaphragm structure section.

By contrast, in the gas sensor of the present invention, the ceramic wiring substrate has a multilayer structure in which the plurality of ceramic dielectric layers are formed such that the inner wiring layers are sandwiched therebetween, thereby enhancing the degree of freedom for wiring between the gas detection element and outer electrodes.

Also, since the recess is formed on the ceramic dielectric layer among the plurality of ceramic dielectric layers on which the gas detection element is mounted, in a region in opposition to the diaphragm structure section, the following problem is prevented: when the gas detection portion undergoes heating control which is performed by use of a microheater or the like formed in the diaphragm structure section, the internal pressure of the diaphragm structure section increases, thereby causing damage to the diaphragm structure section.

Preferably, in the above-described gas sensor, a bottom surface of the ceramic wiring substrate which is located opposite a side where the gas detection element is mounted is formed substantially planar, and outer electrodes to be electrically connected to a circuit board to which the gas sensor is fixedly attached are formed on the bottom surface.

In the gas sensor of the present invention, the bottom surface of the ceramic wiring substrate is formed substantially planar, and the outer electrodes to be connected to the gas detection element are formed on the bottom surface. Thus, the ceramic wiring substrate (gas sensor itself) can be surface-mounted on the circuit board on which the gas sensor is mounted. This can minimize the occupancy rate (the ratio of mounting area) of the gas sensor to be mounted on the circuit board and can simplify the step of mounting the gas sensor on the circuit board.

Preferably, in the above-described gas sensor, a plurality of the gas detection elements which respond to different gas species are mounted on the ceramic wiring substrate.

By means of mounting a plurality of gas detection elements which respond to different gas species on a single ceramic wiring substrate, a plurality of component gases contained in a gas to be measured can be detected without increasing the number of ceramic wiring substrates each functioning as a support member.

Different gas species may specifically include an oxidizing gas such as $NO_x$ and a reducing gas such as CO or HC.

BRIEF DESCRIPTION OF THE DRAWINGS

FIG. 1 is an exploded perspective view of a gas sensor 1 according to an embodiment of the present invention.

FIG. 2 is a plan view of the gas sensor 1.

FIG. 3 is a bottom view of the gas sensor 1.

FIG. 4 is a plan view of a ceramic wiring substrate 2.

FIG. 5 is a sectional view of the ceramic wiring substrate 2 taken along line A-A of FIG. 4 and viewed in the direction of arrows A.

FIG. 6 is a plan view of a gas detection portion 12 of a gas detection element 8.

FIG. 7 is a plan view of the ceramic wiring substrate 2 with a protective cap 3 removed.

FIG. 8 is a sectional view of the ceramic wiring substrate 2 taken along line B-B of FIG. 7 and viewed in the direction of arrows B.

FIG. 9 is a plan view of the ceramic wiring substrate 2 with the protective cap 3 removed.

FIG. 10 is a sectional view of the ceramic wiring substrate 2 taken along line D-D of FIG. 9 and viewed in the direction of arrows D.

FIG. 11 is a sectional view of the gas sensor 1 taken along line C-C of FIG. 2 and viewed in the direction of arrows C.

FIG. 12 is an exploded perspective view of a gas sensor 100 according to another embodiment (modified embodiment) of the present invention.

FIG. 13 is a sectional view of the gas sensor 100 taken along line E-E of FIG. 12.

DESCRIPTION OF REFERENCE NUMERALS 1, 100: gas sensor
2: ceramic wiring substrate
3, 103: protective cap
4: first layer (ceramic dielectric layer)
5: second layer (ceramic dielectric layer)
5A: internal-pressure-adjusting recess
6: third layer (ceramic dielectric layer)
6B, 6D: diaphragm structure section
6E, 6F, 6G: internal-pressure release hole
7: fourth layer (ceramic dielectric layer)
8, 9: gas detection element
12, 13: gas detection portion
12A: sensing electrode
14A to 14D: connection electrode
15A to 15D: connection electrode
16A, 16B, 18A, 18B: connection electrode
17: common electrode
20A to 20D: Au wire
21A to 21D: Au wire
30: ceiling portion
31 to 39: gas inlet (gas intake)
51A to 51F: outer electrode
131 to 137: gas inlet (gas intake)
131A to 137A: nail-like portion
S: gas-measuring space

BEST MODE FOR CARRYING OUT THE INVENTION

A gas sensor 1 according to an embodiment of the present invention will next be described with reference to the drawings. First, the exterior of the gas sensor 1 will be described with reference to FIGS. 1 to 3. FIG. 1 is an exploded perspective view of the gas sensor 1 according to the embodiment of the present invention; FIG. 2 is a plan view of the gas sensor 1; and FIG. 3 is a bottom view of the gas sensor 1. The present invention can be applied to various types of gas sensors for detecting component gases contained in a gas to be measured. The gas sensor 1 of the present embodiment will be described while mentioning, for example, a gas sensor for detecting variation in concentration of a reducing gas such as CO or HC, or an oxidizing gas such as $NO_x$. The gas sensor 1 is installed, for example, in the vicinity of a front grill in an engine room of an automobile and is used as an air-conditioning sensor for detecting variation in the concentration of CO or HC or the concentration of $NO_x$ in environmental gas so as to change over operation modes of an air-conditioning control apparatus between introduction of the outside air and re-circulation of the inside air.

As shown in FIGS. 1 and 2, this gas sensor 1 is formed into a shape resembling a rectangular parallelepiped. A protective cap 3 is attached from above in FIG. 1 to a ceramic wiring substrate 2 in such a manner as to cover an opening portion of a cavity formed on the ceramic wiring substrate 2. The ceramic wiring substrate 2 has a multilayer structure. Gas detection elements 8 and 9 have a diaphragm structure and are mounted in the cavity of the ceramic wiring substrate 2. The protective cap 3 includes a planar ceiling portion 30 and perpendicularly projecting portions 41 and 42 extending downward from the ceiling portion 30 in FIG. 1. The protective cap 3 is formed from a stainless steel plate by pressing. The ceiling portion 30 is formed into a substantially rectangular shape as viewed in plane. The ceiling portion 30 is provided with gas inlets 31, 32, 32, 33, 34, 35, 36, 37, 38, and 39 each having a substantially circular shape as viewed in plane, for introducing a gas to be measured into the interior (cavity) of the gas sensor 1. When the protective cap 3 is attached to the ceramic wiring substrate 2, the protective cap 3 and the ceramic wiring substrate 2 define a gas-measuring space S therebetween. The gas inlets 31 to 39 correspond to the "gas intakes" of the present invention. A gas to be measured is introduced into the gas-measuring space S from the outside through the gas inlets 31 to 39.

As shown in FIG. 3, a bottom surface 1A of the gas sensor 1 (in other words, the bottom surface of the ceramic wiring substrate 2) is formed into a substantially rectangular plane. Substantially rectangular outer electrodes 51A, 51B, 51C, 51D, 51E, and 51F are provided on the bottom surface 1A and are joined by soldering or the like to an unillustrated circuit board. Au plating films, for example, are formed on the surfaces of the outer electrodes 51A, 51B, 51C, 51D, 51E, and 51F.

Next, the structure of the ceramic wiring substrate 2, which partially constitutes the gas sensor 1, will be described in detail with reference to FIGS. 1 and 3 to 5. FIG. 4 is a plan view of the ceramic wiring substrate 2, and FIG. 5 is a sectional view of the ceramic wiring substrate 2 taken along line A-A of FIG. 4 and viewed in the direction of arrows A. As shown in FIGS. 1 and 5, the ceramic wiring substrate 2 has a multilayer structure which has a substantially rectangular shape as viewed in plane and is formed of an $Al_2O_3$ (alumina) sintered body in which four ceramic dielectric layers (alumina dielectric layers); specifically, a first layer 4, a second layer 5, a third layer 6, and a fourth layer 7, from bottom to top in FIG. 1, are laminated. Herein, a side of the ceramic wiring substrate 2 on which the gas detection elements 8 and 9 are mounted is taken as a top surface, and the opposite side is taken as a bottom surface. In other words, in the gas sensor 1 of the present embodiment, the side of the ceramic wiring substrate 2 (multilayer structure) on which the two gas detection elements 8 and 9 are mounted is taken as the top surface, and the opposite side is taken as the bottom surface 1A. Notably, the top surface of the ceramic wiring substrate 2 means a region of the ceramic wiring substrate 2 which is visible when viewed in the direction directed from the top surface toward the bottom surface. Unillustrated inner conductive traces are formed on the surfaces of the first to third layers 4 to 6 of the multilayer structure, thereby forming inner wiring layers.

As shown in FIGS. 1 and 4, recesses 2C, 2D, 2E, 2F, 2G, 2H, 2I, 2J, 2K, 2L, 2M, and 2N each having a substantially arc shape as viewed in plane perpendicular to the direction of lamination of the ceramic wiring substrate 2 are formed on longitudinal side surfaces 2P and 2Q of the ceramic wiring substrate 2 in such a manner as to extend through the first to fourth layers 4 to 7. A guide recess 2A is formed on a lateral side surface (left side surface in FIG. 1) 2S of the ceramic wiring substrate 2 in such a manner as to extend through the first to fourth layers 4 to 7. Also, a guide recess 2B is formed on the other lateral surface (right side surface in FIG. 1) 2R in opposition to the side surface 2S in such a manner as to extend through the first to fourth layers 4 to 7.

As shown in FIGS. 3 and 5, an engagement portion 4A is formed on the lateral side surface 2S of the first layer 4, which is the lowermost layer. The engagement portion 4A is a recess whose depth is greater than that of the guide recess 2A as measured in the longitudinal direction of the ceramic wiring substrate 2. Also, an engagement portion 4B is formed on a right side surface 2R of the first layer 4. The engagement portion 4B is a recess whose depth is greater than that of the guide recess 2B. An engagement projection 41A of the perpendicularly projecting portion 41 and an engagement projection 42A of the perpendicularly projecting portion 42 of the protective cap 3, which will be described later, are fitted for engagement into the engagement potions 4A and 4B, respectively.

Further, as shown in FIGS. 4 and 5, an internal-pressure-adjusting recess 5A for adjusting the internal pressure of the diaphragm structure, which will be described later, is formed in the second layer 5 at a laterally central portion in such a manner as to extend in the longitudinal direction. A through hole which extends through the third layer 6 is formed in the third layer 6 in a central region; a through hole whose opening is greater than that of the through hole of the third layer 6 is formed in the fourth layer 7 in such a manner as to extend through the fourth layer 7; and wall surfaces which define these through holes define a cavity. The plate-like gas detection elements 8 and 9, each of which has a rectangular shape as viewed in plane, are arranged in parallel in the through hole of the third layer 6 and are bonded to the upper surface of the second layer 5. Internal-pressure release holes 6E, 6F, and 6G are formed in the third layer 6 between the gas detection element 8 and the wall surface of the third layer 6 which defines the through hole, between the gas detection elements 8 and 9, and between the gas detection element 9 and the wall surface, respectively. When the pressure in the internal-pressure-adjusting recess 5A increases, air is released from the internal-pressure-adjusting recess 5A to the exterior of the gas sensor through the internal-pressure release holes 6E, 6F, and 6G so as to render the internal pressure of the internal-pressure-adjusting recess 5A equal to the outside air pressure. Further, as shown in FIGS. 1 and 5, the fourth layer 7 is laminated on the third layer 6; and an opening portion 7A which has a substantially rectangular shape as viewed in plane is formed in the fourth layer 7, so that the gas detection elements 8 and 9 are exposed therethrough.

Next, the structure of the gas detection elements 8 and 9 will be described with reference to FIGS. 1 and 4 to 6. FIG. 6 is a plan view of a gas detection portion 12 of the gas detection element 8. The gas detection portions 12 and 13 each of which has a substantially square shape as viewed in plane and detects a component gas of a gas to be measured are formed in the gas detection elements 8 and 9, respectively, and, as shown in FIG. 5, recess portions 6A and 6C are formed in the gas detection elements 8 and 9 behind the gas detection portions 12 and 13, respectively, thereby forming diaphragm structure sections 6B and 6D. An unillustrated microheater formed of a Pt conductive-trace is incorporated in each of the diaphragm structure sections 6B and 6D. As shown in FIG. 4, the gas detection portion 12 is provided on the upper surface of the gas detection element 8 having an elongated substantially rectangular shape while being offset toward the rear side surface 2Q. The gas detection portion 13 is also provided similarly on the upper surface of the gas detection element 9. As shown in FIG. 6, the gas detection portion 12 of the gas detection element 8 has a substantially square shape as viewed in plane, and sensing electrodes 12A formed in contact with an unillustrated gas sensitive film are provided in a central region of the gas detection portion 12. The gas detection portion 13 also has a structure similar to that of the gas detection portion 12.

Further, electrode pads for connection electrodes 14A, 14B, 14C, and 14D are formed on the upper surface of the gas detection element 8 in a region which is offset toward the front side surface 2P of the gas detection element 8 (in a region which is offset toward the near side in FIG. 4). The connection electrodes 14A to 14D are adapted to lead out an output of the gas detection element 8 and to supply power to the gas detection element 8. Similarly, electrode pads for connection electrodes 15A, 15B, 15C, and 15D are formed on the upper surface of the gas detection element 9 in a region which is offset toward the front side surface 2P of the gas detection element 9. Further, electrode pads for connection electrodes 16A, 16B, 18A, and 18B and a common electrode 17 are formed on the upper surface of the third layer 6 in the vicinity of the connection electrodes 14A to 14D and 15A to 15D. The connection electrodes 14A, 14B, 15C, and 15D are wire-bonded to the corresponding connection electrodes 16A, 16B, 18A, and 18B by use of Au wires 20A, 20B, 21C, and 21D, respectively. The connection electrodes 14C, 14D, 15A, and 15B are wire-bonded to the common electrode 17 by use of Au wires 20C, 20D, 21A, 21B, respectively. The connection electrodes 14A to 14D and 15A to 15D correspond to the "element-side electrodes" of the present invention, and the connection electrodes 16A, 16B, 18A, and 18B and the common electrode 17 correspond to the "substrate-side electrodes" of the present invention. The Au wires 20A, 20B, 21C, and 21D correspond to the "connection portions" of the present invention.

Next, a manufacturing process for the first to fourth layers 4 to 7 of the above-described ceramic wiring substrate 2 will be described. First, an $Al_2O_3$ (alumina) green sheet is cut into sheets each having an appropriate size for use in the manufacturing process. A large number of individual layers of the ceramic wiring substrate 2 are to be arrayed on each of the thus-prepared sheets. Specifically, there are manufactured a sheet (hereinafter called a "first layer sheet") on which a large number of first layers 4 are arrayed, a sheet (hereinafter called a "second layer sheet") on which a large number of second layers 5 are arrayed, a sheet (hereinafter called a "third layer sheet") on which a large number of third layers 6 are arrayed, and a sheet (hereinafter called a "fourth layer sheet") on which a large number of fourth layers 7 are arrayed. Next, a wiring pattern which is to become an inner wiring layer is printed on each of the first to third layer sheets in a green condition by use of W (tungsten) paste. Then, the first to fourth layer sheets are laminated and compression-bonded, thereby forming a multilayer sheet. Next, cutting grooves are formed on the compression-bonded multilayer sheet so as to facilitate division into individual pieces after firing. Subsequently, the multilayer sheet is cut into pieces each having a size suited for firing, followed by debindering and then firing. Next, Ni plating, Au plating, and the like are performed on the electrodes. The thus-prepared sheets are each divided into individual ceramic wiring substrates 2 after being checked for electrical properties, current leak property, appearance, etc.

Next, a manufacturing process for the gas detection elements 8 and 9 will be briefly described. First, a silicon wafer which serves as a substrate for the gas detection elements 8 and 9 is cleaned. Then, a silicon oxide film is formed on the silicon wafer, and a silicon nitride film is formed thereon. Next, microheaters are formed. For instance, after a Ta layer is formed by sputtering, a Pt layer is formed. The Pt layer is subjected to patterning by photolithography, followed by etching so as to form the microheaters. Subsequently, a silicon nitride film is formed in such a manner as to cover the microheaters. Then, microheater contact portions are formed at end portions of the microheaters. For instance, the silicon nitride film is subjected to etching so as to form the microheater contact portions. Next, sensing electrodes are formed above the microheaters. For instance, after a Ti layer is formed by sputtering, a Pt layer is formed. The Pt layer is subjected to patterning by photolithography, followed by etching so as to form the sensing electrodes. Then, contact pads (connection electrodes 14A to 14D and 15A to 15D) are formed at end portions of the sensing electrodes and at end portions of the microheaters. For instance, after a Cr layer is formed by sputtering, an Au layer is formed. The Au layer is subjected to patterning by photolithography, followed by etching so as to form the connection electrodes 14A to 14D and 15A to 15D. Next, silicon is subjected to anisotropic etching so as to form the diaphragm structure sections 6B and 6D and the gas sensitive film formed of a metal oxide semiconductor which predominantly contains $SnO_2$. Subsequently, the silicon wafer is cut to obtain the gas detection elements 8 and 9.

Next, a seal member 61 for protecting the connection electrodes 14A to 14D and 15A to 15D, the connection electrodes 16A, 16B, 18A, and 18B, the common electrode 17, and the Au wires 20A to 20D and 21A to 21D will be described with reference to FIGS. 7 and 8. FIG. 7 is a plan view of the ceramic wiring substrate 2 with the protective cap 3 removed. FIG. 8 is a sectional view of the ceramic wiring substrate 2 taken along line B-B of FIG. 7 and viewed in the direction of arrows B. Although unillustrated in FIGS. 1 and 4, as shown in FIGS. 7 and 8, the seal member 61 is provided on the ceramic wiring substrate 2 for protecting the connection electrodes 14A to 14D and 15A to 15D of the gas detection elements 8 and 9, which are bonded onto the second layer 5 by means of an adhesive 62, and the connection electrodes 16A, 16B, 18A, and 18B and the common electrode 17, which are formed on the third layer 6, and the Au wires 20A to 20D and 21A to 21D. The seal member 61 is of a synthetic resin (e.g., epoxy resin) which fills a space between the fourth layer 7 and a dam member 60, which is bonded to the gas detection elements 8 and 9 between the gas detection portions 12 and 13 and the connection electrodes 14A to 14D and 15A to 15D; is made of a synthetic resin (e.g., epoxy resin); and has a cross section resembling that of a semicylinder. The seal member 61 is fluid before solidification and is solidified after being charged into the space between the dam member 60 and the fourth layer 7. The dam member 60 prevents the seal member 61 before solidification from flowing and adhering to the gas detection portions 12 and 13 of the gas detection elements 8 and 9, respectively.

The seal member 61 seals in for protection the connection electrodes 14A to 14D and 15A to 15D, the connection electrodes 16A, 16B, 18A, and 18B, the common electrode 17, and the Au wires 20A to 20D and 21A to 21D. Thus, the connection electrodes 14A to 14D and 15A to 15D, the connection electrodes 16A, 16B, 18A, and 18B, the common electrode 17, and the Au wires 20A to 20D and 21A to 21D are free from damage and short circuit which could otherwise result from foreign matter.

Next, the ceramic wiring substrate 2 using a seal member 63, which is a modified embodiment of the above-described seal member 61, will be described with reference to FIGS. 9 and 10. FIG. 9 is a plan view of the ceramic wiring substrate 2 with the protective cap 3 removed, and FIG. 10 is a sectional view of the ceramic wiring substrate 2 taken along line D-D of FIG. 9 and viewed in the direction of arrows D. The ceramic wiring substrate 2 uses the seal member 63. In contrast to the seal member 61, the seal member 63 is of a resin which has high viscosity; i.e., low fluidity, even before solidification (for example, epoxy resin having high viscosity). Accordingly, as shown in FIGS. 9 and 10, the seal member 63 does not require the dam member 60 adapted to prevent adhesion thereof to the gas detection portions 12 and 13 of the gas detection elements 8 and 9. Only the seal member 63 is employed to seal in for protection the connection electrodes 14A to 14D and 15A to 15D, the connection electrodes 16A, 16B, 18A, and 18B, the common electrode 17, and the Au wires 20A to 20D and 21A to 21D. Accordingly, there is no need to bond the dam member 60 onto the gas detection elements 8 and 9.

Next, the structure of the protective cap 3 will be described with reference to FIGS. 1 to 3 and FIG. 11. FIG. 11 is a sectional view of only the protective cap 3 of the gas sensor 1 taken along line C-C of FIG. 2 and viewed in the direction of arrows C. As shown in FIGS. 1, 2, and 11, the protective cap 3 is formed from a stainless steel plate by pressing as mentioned previously and includes the ceiling portion 30, which has a substantially rectangular shape as viewed in plane, and the perpendicularly projecting portions 41 and 42, which are bent downward from corresponding longitudinal end faces of the ceiling portion 30, perpendicularly to the ceiling portion 30 and along the corresponding side surfaces of the ceramic wiring substrate 2. Each of the perpendicularly projecting portions 41 and 42 has a rectangular plate shape. The engagement projections 41A and 42A are formed by pressing at lower end portions of the perpendicularly projecting portions 41 and 42, respectively, in an inward projecting condition. As shown in FIGS. 3 and 11, the engagement projections 41A and 42A are fitted into the engagement portions 4A and 4B, respectively, which are provided on the two opposed side surfaces of the ceramic wiring substrate 2.

In attachment of the protective cap 3 to the ceramic wiring substrate 2, the perpendicularly projecting portions 41 and 42 are pressed into the guide recesses 2A and 2B, which are provided on the longitudinally opposed side surfaces of the ceramic wiring substrate 2, while being guided by the guide recesses 2A and 2B, until the back surface of the ceiling portion 30 of the protective cap 3 abuts the upper surface of the fourth layer 7. The engagement projections 41A and 42A provided on the perpendicularly projecting portions 41 and 42, respectively, are fitted into the engagement portions 4A and 4B, respectively. In this condition, the protective cap 3 is fixedly attached to the ceramic wiring substrate 2, whereby the gas-measuring space S is formed between the same and the ceramic wiring substrate 2.

Next, the arrangement of the gas inlets 31 to 39 formed in the ceiling portion 30 of the protective cap 3 will be described. As shown in FIGS. 1 and 2, the gas inlets 31 to 39, each of which has a substantially circular shape and through which a gas to be measured enters the interior (gas-measuring space S) of the gas sensor 1, are formed in the ceiling portion 30 of the protective cap 3 in such a manner as to extend through the ceiling portion 30. The gas inlets 31 to 39 are not provided at random, but are provided such that when the gas inlets 31 to 39 and the diaphragm structure sections 6B and 6D are orthogonally projected onto a plane formed by horizontally extending the surface of the gas detection elements 8 and 9, the orthogonally projected images of the gas inlets 31 to 39 do not overlap with those of the diaphragm structure sections 6B and 6D; i.e., the gas inlets 31 to 39 are arranged in such a manner as to avoid being located above the gas detection portions 12 and 13 of the diaphragm structure.

In other words, the gas inlets 31 to 39 are arranged on the ceiling portion 30 of the protective cap 3 such that when the ceiling portion 30 of the protective cap 3 is viewed vertically from above, the gas detection portions 12 and 13 are invisible through the gas inlets 31 to 39. Accordingly, even when foreign matter drops in environmental gas (gas to be measured) and passes through the gas inlets 31 to 39, the foreign matter does not directly impinge on the gas detection portions 12 and 13, thereby preventing adhesion of the foreign matter to the gas detection portions 12 and 13, and damage to the very thin diaphragm structure sections 6B and 6D which could otherwise result from impingement of the foreign matter. As mentioned above, in the gas sensor 1 of the present embodiment, a plurality of gas inlets 31 to 39 are formed such that when each of the gas inlets 31 to 39 is viewed from the outside of the ceiling portion 30 along a direction perpendicular to the mounting surface of the ceramic wiring substrate 2 on which the gas detection elements 8 and 9 are mounted, the diaphragm structure sections 6B and 6D of the gas detection elements 8 and 9 are invisible through the gas inlets 31 to 39.

Further, a planar portion 30A is formed on the ceiling portion 30 of the protective cap 3, and a vacuum chuck nozzle of a chip mounter can abut the planar portion 30A. Accordingly, in the gas sensor 1, the ceiling portion 30 of the protective cap 3 has the planar portion 30A which the vacuum-chuck nozzle of a chip mounter can abut, and the bottom surface 1A of the first layer 4 of the ceramic wiring substrate 2 is formed into a substantially rectangular plane and has the substantially rectangular outer electrodes 51A to 51F formed thereon. Thus, the size of the gas sensor 1 can be reduced, and the gas sensor 1, together with electronic components, can be surface-mounted on a circuit board by use of a chip mounter.

Further, the gas inlets 31 to 39 provided on the ceiling portion 30 of the protective cap 3 are arranged such that when the gas inlets 31 to 39 and the Au wires 20A to 20D and 21A to 21D, which serve as connection portions, are orthogonally projected onto a plane formed by horizontally extending the surface of the gas detection elements 8 and 9, the orthogonally projected images of the gas inlets 31 to 39 do not overlap with those of the Au wires 20A to 20D and 21A to 21D, which serve as connection portions; i.e., the gas inlets 31 to 39 are arranged in such a manner as to avoid being located above the Au wires 20A to 20D and 21A to 21D (connection portions). By this procedure, foreign matter which has entered the interior of the gas sensor 1 through the gas inlets 31 to 39 is unlikely to adhere to the Au wires 20A to 20D and 21A to 21D, and a short circuit which could otherwise arise between the Au wires 20A to 20D and 21A to 21D, which serve as connection portions, as a result of adhesion of foreign matter, can be prevented. As mentioned above, in the gas sensor 1 of the present embodiment, a plurality of gas inlets 31 to 39 are formed such that when each of the gas inlets 31 to 39 is viewed from the outside of the ceiling portion 30 along a direction perpendicular to the mounting surface of the ceramic wiring substrate 2 on which the gas detection elements 8 and 9 are mounted, the Au wires 20A to 20D and 21A to 21D, which serve as connection portions, are invisible through the gas inlets 31 to 39.

Notably, as shown in FIG. 2, the gas inlets 31 to 39 may be arranged such that the orthogonally projected images of the gas inlets 31 to 39 do not overlap with those of the Au wires 20A to 20D and 21A to 21D, which serve as connection portions, those of the connection electrodes 14A to 14D and 15A to 15D, those of the connection electrodes 16A, 16B, 18A, and 18B, and that of the common electrode 17. In this case, foreign matter which has entered the interior of the gas sensor 1 through the gas inlets 31 to 39 is unlikely to adhere to not only the Au wires 20A to 20D and 21A to 21D but also the connection electrodes 14A to 14D and 15A to 15D, the connection electrodes 16A, 16B, 18A, and 18B, and the common electrode 17, and these electrodes are free from a short circuit which could otherwise result from adhesion of foreign matter.

Further, as shown in FIG. 2, the protective cap 3 has a recess 40 for confirming orientation of the gas sensor 1 when the gas sensor 1 is to be mounted on an unillustrated circuit board. The recess 40 is formed such that when the protective cap 3 is viewed in plane, the recess 40 has an arc shape and is located on a long side of the protective cap 3 while being offset toward the left from a central portion of the long side.

Modified Embodiment

Next, a gas sensor 100 according to another embodiment of the present invention will be described with reference to FIGS. 12 and 13. The gas sensor 100 is similar to the gas sensor 1 according to the above-described embodiment except for the form of the gas inlets 31 to 39 of the protective cap 3 shown in FIGS. 1 and 2. Thus, only different features are described, and the description of similar features is omitted or briefed.

When the protective cap 103 which partially constitutes the gas sensor 100 of the present embodiment is attached to the ceramic wiring substrate 2, the protective cap 103 and the ceramic wiring substrate 2 define the gas-measuring space S therebetween. The protective cap 103 includes the ceiling portion 30 and the perpendicularly projecting portions 41 and 42. A plurality of gas inlets 131 to 137 are formed in the ceiling portion 30 of the protective cap 103. In this protective cap 103, linear slits are formed in the ceiling portion 30 which has a substantially rectangular shape as viewed in plane, in parallel with the longitudinal direction of the ceiling portion 30. Portions of the outer wall extending from the slits are deformed to project toward the gas-measuring space S while being integral at their ends with the outer wall (planar portion 30A) of the ceiling portion 130, thereby forming the gas inlets 131 to 137 having nail-like portions 131A to 137A, respectively.

In the gas sensor 100 according to the present embodiment, a gas to be measured is introduced into the gas-measuring space S from the outside of the gas sensor 100 along the nail-like portions 131A to 137A through the gas inlets 131 to 137. The gas detection elements 8 and 9 mounted on the ceramic wiring substrate 2 detect variation in concentrations of specific component gases contained in the gas to be measured. Notably, in the gas sensor 100, since the gas inlets 131 to 137 having the nail-like portions 131A to 137A, respectively, are formed in the ceiling portion 30 of the protective cap 103, when the ceiling portion 30 of the protective cap 103 is viewed vertically from above, the gas detection elements 8 and 9 and the Au wires 20A to 20D and 21A to 21D, which serve as connection portions, are invisible through the gas inlets 131 to 137.

Accordingly, even when foreign matter drops in environmental gas (gas to be measured) and passes through the gas inlets 131 to 137, the foreign matter does not directly impinge on the gas detection portions 12 and 13 and the Au wires 20A to 20D and 21A to 21D, which serve as connection portions, thereby preventing adhesion of the foreign matter to the gas detection portions 12 and 13, and damage to the very thin diaphragm structure sections 6B and 6D which could otherwise result from impingement of the foreign matter. Also, adhesion of foreign matter to the above-mentioned connection portions can be prevented, thereby preventing a short circuit between the connection portions. As mentioned above, also in the gas sensor 100 of the present embodiment, a plurality of gas inlets 131 to 137 are formed such that when each of the gas inlets 131 to 137 is viewed from the outside of the ceiling portion 30 along a direction perpendicular to the mounting surface of the ceramic wiring substrate 2 on which the gas detection elements 8 and 9 are mounted, the diaphragm structure sections 6B and 6D of the gas detection elements 8 and 9 and the Au wires 20A to 20D and 21A to 21D, which serve as connection portions, are invisible through the gas inlets 131 to 137. The above-mentioned gas inlets 131 to 137 correspond to the "gas intakes" of the present invention.

While the present invention has been described with reference to the above embodiments, the present invention is not limited thereto, but may be modified as appropriate without departing from the spirit or scope of the invention.

For example, the ceramic wiring substrate 2 of the gas sensor 1 has a multilayer structure of four layers. However, the number of layers is not limited to four. The number of layers may be 2, 3, 5, 6, or the like so long as a multilayer structure is established. The gas sensor 1 has two gas detection elements incorporated therein. However, the number of gas detection elements may be one or three. No limitation is imposed on material for the gas detection portions 12 and 13 formed on the gas detection elements 8 and 9, respectively so long as the gas detection portions 12 and 13 can detect specific component gases contained in a gas to be measured. Also, the gas detection portions 12 and 13 may be of a thick film or a thin film.

The invention claimed is:

1. A gas sensor comprising:
a gas detection element;
a ceramic wiring substrate on which the gas detection element is mounted; and
a protective cap which is directly attached to the ceramic wiring substrate in such a manner as to cover the gas detection element, the protective cap is made of metal and defines, when attached to the ceramic wiring substrate, a gas-measuring space in cooperation with the ceramic wiring substrate, and has a gas intake for introducing gas to be measured into the gas measuring space from the outside thereof;
wherein the gas detection element is mounted in a cavity of the ceramic wiring substrate;
wherein the gas detection element includes a diaphragm structure section which is formed of a silicon substrate, and the diaphragm structure section includes a gas detection portion;
wherein the ceramic wiring substrate has a multilayer structure in which a plurality of ceramic dielectric layers are laminated; a recess is formed on a portion of a side surface of the ceramic wiring substrate which corresponds to a side surface of a ceramic dielectric layer other than an uppermost ceramic dielectric layer which forms a top surface of the ceramic wiring substrate;
wherein the protective cap is held on the ceramic wiring substrate in a nonadhering condition; and
wherein the protective cap has a perpendicularly projecting portion extending along the side surface of the ceramic wiring substrate; and an engagement projection to be fitted into the recess is formed on the perpendicularly projecting portion.

2. A gas sensor according to claim 1, wherein the ceramic wiring substrate has a substantially quadrangular shape as viewed along the direction of lamination of the multilayer structure and the recess is formed on each of at least two opposed side surfaces of the ceramic wiring substrate.

3. A gas sensor according to claim 1, a guide recess is formed on the side surfaces of the ceramic wiring substrate so as to guide the perpendicularly projecting portions to locations where the engagement projections are fitted into the corresponding recesses.

4. A gas sensor according to claim 1, wherein the gas detection element includes a diaphragm structure section, and the diaphragm structure section includes a gas detection portion;

the protective cap has a plurality of the gas intakes formed in a ceiling portion in opposition to a mounting surface of the ceramic wiring substrate on which the gas detection element is mounted; and the plurality of gas intakes are formed such that when the gas intakes are viewed from the outside of the ceiling portion along a direction perpendicular to the mounting surface, the diaphragm structure section of the gas detection element is invisible therethrough.

5. A gas sensor according to claim 4, wherein element-side electrodes are provided on the gas detection element;

substrate-side electrodes are provided on the ceramic wiring substrate;

connection portions are provided for connecting the element-side electrodes and the corresponding substrate side electrodes; and the plurality of gas intakes are formed such that when the gas intakes are viewed from the outside of the ceiling portion along a direction perpendicular to the mounting surface, the connection portions are invisible therethrough.

6. A gas sensor according to claim 1, wherein the ceramic wiring substrate has a multilayer structure in which a plurality of ceramic dielectric layers are formed such that inner wiring layers are sandwiched therebetween; and wherein the recess is formed on the ceramic dielectric layer among the plurality of ceramic dielectric layers on which the gas detection element is mounted, in a region in opposition to the diaphragm structure section.

7. A gas sensor according to claim 1, wherein a bottom surface of the ceramic wiring substrate which is located opposite a side where the gas detection element is mounted is formed substantially planar, and outer electrodes to be electrically connected to a circuit board to which the gas sensor is fixedly attached are formed on the bottom surface.

8. A gas sensor according to claim 1, wherein a plurality of gas detection elements which respond to different gas species are mounted on the ceramic wiring substrate.

* * * * *